US010661253B2

(12) United States Patent
Asthana et al.

(10) Patent No.: US 10,661,253 B2
(45) Date of Patent: May 26, 2020

(54) METHOD OF PREPARATION OF MIXED METAL OXIDE USING GLUCOSE OXIDATION ASSISTED PRECIPITATION

(71) Applicant: BHARAT PETROLEUM CORPORATION LTD., Uttar Pradesh (IN)

(72) Inventors: Sonal Asthana, Uttar Pradesh (IN); Chanchal Samanta, Uttar Pradesh (IN); Ravi Kumar Voolapalli, Uttar Pradesh (IN); Sanjay Bhargava, Uttar Pradesh (IN); Basudeb Saha, Delhi (IN)

(73) Assignee: BHARAT PETROLEUM CORPORATION, Uttar Pradesh (IN)

( * ) Notice: Subject to any disclaimer, the term of this patent is extended or adjusted under 35 U.S.C. 154(b) by 0 days.

(21) Appl. No.: 15/409,382

(22) Filed: Jan. 18, 2017

(65) Prior Publication Data
US 2017/0203281 A1 Jul. 20, 2017

(51) Int. Cl.
B01J 23/80 (2006.01)
C07C 41/09 (2006.01)
(Continued)

(52) U.S. Cl.
CPC ............ B01J 23/80 (2013.01); B01J 21/04 (2013.01); B01J 35/0006 (2013.01); B01J 37/009 (2013.01); B01J 37/0063 (2013.01); B01J 37/031 (2013.01); B01J 37/04 (2013.01); B01J 37/06 (2013.01); C01G 1/02 (2013.01); C01G 3/02 (2013.01); C01G 9/00 (2013.01); C01G 9/006 (2013.01); C07C 29/1518 (2013.01); C07C 41/09 (2013.01); C01P 2002/72 (2013.01)

(58) Field of Classification Search
CPC ........ B01J 23/80; B01J 21/04; B01J 35/0006; B01J 37/031; B01J 37/04; B01J 37/009; B01J 37/06; B01J 37/0063; C01C 41/09; C01C 29/1518; C01G 9/006
See application file for complete search history.

(56) References Cited

U.S. PATENT DOCUMENTS 4,113,658 A * 9/1978 Geus .................. B01J 37/031
252/62.55

FOREIGN PATENT DOCUMENTS

CN          102321879 A  *  1/2012

OTHER PUBLICATIONS

CN 102321879 A machine translation.*

* cited by examiner

Primary Examiner — James A Fiorito
(74) Attorney, Agent, or Firm — Seyfarth Shaw LLP

(57) ABSTRACT

The present invention provides a process for in-situ preparation of metal oxide(s) comprising the step of precipitating a metal salt solution with Fehling's reagent B and glucose at a suitable temperature. The metal oxide(s) prepared according to the present invention can be used for diverse applications including their utility as catalyst(s) in one or more reactions. The present invention further provides a highly selective bi-functional hybrid catalyst for direct conversion of syn-gas to dimethyl ether (DME) and methods of preparation thereof. The one or more metal oxide(s) can be directly obtained from the metal precursors following the method(s) of the present invention instead of metal hydroxides as in conventional known methods, thereby eliminating the necessity of high temperature calcination step(s) and rigorous reduction procedure(s).

6 Claims, 1 Drawing Sheet

(51) Int. Cl.
*C07C 29/151* (2006.01)
*C01G 9/00* (2006.01)
*B01J 21/04* (2006.01)
*B01J 35/00* (2006.01)
*B01J 37/03* (2006.01)
*B01J 37/04* (2006.01)
*B01J 37/00* (2006.01)
*B01J 37/06* (2006.01)
*C01G 3/02* (2006.01)
*C01G 1/02* (2006.01)

METHOD OF PREPARATION OF MIXED METAL OXIDE USING GLUCOSE OXIDATION ASSISTED PRECIPITATION

FIELD OF THE INVENTION

The present invention relates to the method of preparation of mixed metal oxide using glucose oxidation assisted precipitation through Fehling's route. The method(s) according to the disclosure can be used to prepare diverse range of products including catalyst(s) with utility in variety of reactions, adsorbents, sensors, carriers, glass, abrasives, ceramics and coatings.

BACKGROUND OF THE INVENTION

Background description includes information that may be useful in understanding the present invention. It is not an admission that any of the information provided herein is prior art or relevant to the presently claimed invention, or that any publication specifically or implicitly referenced is prior art.

Today, majority of mixed metal oxides are prepared through precipitation and co-precipitation methods followed by calcination(s) and subsequent reduction(s). Preparation of metal oxides through conventional precipitation method involves multiple high temperature steps like calcinations(s) and reduction, and these metal oxides are often activated at higher temperatures in case of their utility as bulk catalysts. Such bulk catalysts are used in production of bulk commodity chemicals such as methanol, syn-gas, hydrogen, ammonia, nitric acid, etc. Further, such bulk catalysts can also be used in synthesis of compounds of medicinal interest including drug molecules, apart from their use in synthesis of organic and inorganic molecules. A person skilled in the art would immediately realize the broad range of applications of metal oxides including in catalyst carrier(s), adsorbents, sensors, drug-delivery carriers, glass, abrasives, ceramics and coatings, in FCC and polymerization catalysis and various organic synthesis reactions.

Methanol is one of the top ten versatile chemical primarily produced from natural gas and naphtha. Apart from being itself a fuel and gasoline fuel additives, a numerous chemicals and chemical intermediates such as formaldehyde, acetic acid, MTBE/FAME, methyl acrylate, dimethyl ether (DME), chloromethane, methylamines etc. can be produced from methanol. In addition, olefins such as ethylene and propylene can be manufactured through methanol to olefins (MTO) and methanol to propylene (MTP) process, respectively. Demand for methanol is increasing rapidly. By 2016, global demand for methanol will reach at 92.3 million tons from 55.4 million tons in 2011 and as per IHS estimate, the demand for methanol will reach at 160 million tons by 2020.

Methanol is produced by converting syn-gas, obtained from steam methane reforming of natural gas, coal or biomass gasification through catalytic process. This process employs metal oxide based catalyst comprising of Cu, Zn and Al and prepared through co-precipitation method. The co-precipitation method employs metal salt of Cu, Zn and Al and Na, K hydroxides, carbonate as precipitating agent.

Dimethyl ether (DME), an important derivative of methanol, is increasingly gaining more importance as an alternative fuel because of its numerous advantages over the conventional crude oil derived fuels viz. petrol, diesel. Conventionally, DME is produced through two-step process. The first step is the catalytic conversion of syn-gas to methanol and the second step is dehydration of methanol over an acidic material such as alumina, silica-alumina or zeolite based materials which are bulk catalysts. Because of the very low equilibrium conversion of syn-gas to methanol, direct conversion of syn-gas to DME (STD) has inherent thermodynamic advantage to promote higher syn-gas conversion and thus overall economy of the process. However, embedding two reactors in a single reactor possesses significant challenges in the process. Moreover, since methanol formation and methanol dehydration have different reaction mechanisms, tuning catalytic sites for both the reactions through bi-functional and hybrid catalyst system need great and dedicated efforts.

Direct synthesis of DME from syngas requires bi-functional catalysts having two different active sites; one for methanol formation and the other for methanol dehydration. The prior art discloses that methanol formation from syn-gas is catalyzed by Cr, Cu and other active metals with preferably Cu as metal of choice. On the other hand, dimethyl ether formation from methanol is a dehydration reaction and proceeds through acid catalyzed reaction. The prior art discloses that various metal oxides such as alumina, silica, and mixed metal oxides such as silica-alumina, alumina-titania, alumina-zirconia, zeolites such as H-ZSM-5, H-beta, SAPO etc. are used for dehydration to methanol to DME. The direct conversion of syn-gas to dimethyl ether requires both metallic and dehydrating functions to be incorporated in a single catalyst entity as a hybrid catalyst. The second, third metal can be introduced in the first component of the hybrid catalyst during synthesis of the first component separately. These components may be added as geometrical spacers, structural promoter or catalyst filler with respect to active components such as alumina, zirconium, platinum, magnesium, calcium, manganese, gallium etc. as promoters.

Currently, preparation of first component of catalytic system (methanol synthesis part) for direct DME synthesis from syn-gas is carried out by co-precipitation of metal nitrate salts and a precipitating agent (usually sodium carbonate or sodium hydroxide). The catalyst obtained in the form of hydroxides or hydroxycarbonate as precursors which goes through a series of steps including (i) washing to ensure there is no residual ions; (ii) drying to make sure that all the excess water can be removed; (iii) calcination to convert the catalyst from hydroxides or hydroxycarbonate to metal oxides (in the state of the art methods of preparation, oxide of Cu is obtained as Cupric oxide, Cu (II)O); and (iv) reduction to convert the CuO in the form of $Cu^0$ (active species for methanol synthesis).

The state-of-the-art copper based methanol synthesis catalyst has limitations and disadvantages such as large amount of solvent (i.e water) required for preparing the metal salt solution and to wash the precipitate; high temperature calcination required to convert copper/zinc/aluminium mixed hydroxide precursor to copper oxide/zinc oxide/aluminum oxide state; and need of rigorous hydrogen treatment to convert Cu(II) oxide to Cu(I) and then to Cu(0).

U.S. Pat. No. 2,400,959 discloses a method of preparation of a form of cuprous oxide which was found to be an active catalytic agent for hydrogenation or dehydrogenation of various organic compounds. Here solution of some water soluble copper salt was used, preferably cupric nitrate because of its higher solubility. Halogen salts of copper tend to produce a catalyst of lower activity because traces of the halogen salt remain in the precipitate and tend to sinter under hydrogenating conditions. Also, some other promoters were used along with glucose and NaOH. However the catalyst cuprous oxide obtained was catalytically inactive before applying activation procedures.

Further, US patent publication no. US20110105306 discloses a method for fabricating Cu—Zn—Al catalyst for producing methanol and dimethyl ether using a sol-gel method where crystal grain size, crystal type, surface structure and active sites distribution of the catalyst can be adjusted. Thus overall performance of the catalyst was improved. US2013/0211148 A1 discloses a catalyst comprising several types of combination of well known oxides for methanol/DME synthesis viz. CuO, ZnO, $ZrO_{22}$ and some unpopular oxides viz. boron oxide, niobium oxide, tantalum oxide, phosphorous oxide along with the gamma alumina. The performance of the catalyst synthesized using different combinations of these oxides was found to be outstanding. However, these prior arts use rigorous calcination and reduction steps at very high temperature which makes the catalyst unstable.

There is other literature reported describing the synthesis of catalysts for methanol/DME synthesis but none of them were brought to their final form without performing calcination and directly obtaining oxide form immediately after precipitation. Thus, there is a continuous need and scope in the art of mixed metal oxide synthesis comprising better physical properties, superior stability and improved shelf life without affecting their performance in the participating reactions.

There is thus a need in the art to develop a novel method of preparation of mixed metal oxides which can eliminate the need of calcinations and rigorous reduction procedures.

The present invention satisfies the existing needs, as well as others, and generally overcomes the deficiencies found in the prior art.

Objects of the Invention

It is an object of the present invention to provide a method for in-situ preparation of mixed metal oxide(s) at low temperature through Fehling's solution using sodium potassium tartrate as a metal complexing agent.

A further object of the present invention is to provide a process for in-situ preparation of mixed metal oxide(s) including the step of: precipitating a mixed metal salt solution with Fehling's reagent B and glucose at a suitable temperature; wherein said mixed metal salt solution comprises at least two metal ions; and wherein half cell reduction potential of at least one metal ion of said at least two metal ions is lower than glucose. A further object of the present invention is to provide a process for preparing mixed metal oxide(s), wherein at least one metal ion can be selected from a group consisting of Zn, Mg, Ce, Ga, Al, Zr, Ca or Ti.

A further object of the present invention is to provide a process for preparing mixed metal oxide(s) capable of eliminating the necessity of isolation of one or more metal hydroxide(s). A further object of the present invention is to provide a process for preparing mixed metal oxide(s) capable of eliminating the necessity of calcination(s) and heating at high temperature(s). A further object of the present invention is to provide a process for preparing mixed metal oxide(s) capable of eliminating the necessity of rigorous reduction step(s).

A further object of the present invention is to provide a process for preparing mixed metal oxide(s) that can utilize sub-stoichiometric amount of sodium potassium tartrate in Fehling's reagent B with respect to the metal ions present in the mixed metal salt solution to induce defects and dislocations in the mixed metal oxide(s).

A further object of the present invention is to provide a method for controlled release of metal from a complexing agent so that targeted catalyst with metal oxide(s) in intermediate oxidation state can be obtained.

Another object of the present invention is to provide mixed metal oxide(s) that can be used as catalyst(s) for production of chemicals such as methanol, DME, higher hydrocarbons and the like from syn-gas. A further object of the present invention is to provide mixed metal oxide(s) that can be used as catalyst(s) in Fischer Tropsch synthesis or Water gas shift reaction. A further object of the present invention is to provide mixed metal oxide(s) that can be used as a component for making hybrid catalyst(s). A further object of the present invention is to provide mixed metal oxide(s) that can be used for preparation of bi-functional hybrid catalyst(s).

A further object of the present invention is to provide a process for preparing a bi-functional catalyst wherein at least one metal oxide can be in an intermediate oxidation state, for example, copper oxide in the form of cuprous oxide [Cu(I)O] instead of cupric oxide [Cu(II)O].

A further object of the present invention is to provide a highly selective bi-functional hybrid catalyst that can be used for direct conversion of syn-gas to dimethyl ether (DME). A further object of the present invention is to provide a catalyst component of the hybrid catalyst for the conversion of syn-gas to methanol.

Another object of the present invention is to provide a method of preparation of a superior bi-functional catalyst for direct conversion of syn-gas to DME which can withstand the severe process conditions and resist the coke formation during conversion of syngas to DME.

A further object of the present invention is to provide a process for preparing a bi-functional catalyst capable of exhibiting high stability against sintering and deactivation. A further object of the present invention is to provide a process for preparing a bi-functional catalyst capable of exhibiting high methanol and DME selectivity as well as yield. A further object of the present invention is to provide a process for preparing a bi-functional catalyst capable of involving low process parameter of pressure and temperature.

Another object of the present invention is to provide a process for preparing a mixed metal oxide which obviates the disadvantages associated with known art.

Another object of the present invention is to provide a process for preparing a mixed metal oxide which is inexpensive, dependable and fully effective in accomplishing its intended purposes.

Yet another object of the present invention is to provide a process that is technically and commercially feasible.

Other objects of the present invention will be apparent from the description of the invention herein below.

SUMMARY OF THE INVENTION

The present invention generally relates to in-situ preparation of mixed metal oxide(s) using glucose oxidation assisted precipitation through Fehling's route.

The present invention further relates to a process for in-situ preparation of mixed metal oxide(s) comprising the step of: precipitating a mixed metal salt solution with Fehling's reagent B and glucose at a suitable temperature; wherein said mixed metal salt solution comprises at least two metal ions; and
wherein half cell reduction potential of at least one metal ion of said at least two metal ions is lower than glucose.

In one embodiment, at least one metal ion can be selected from the group consisting of Zn, Mg, Ce, Ga, Al, Zr, Ca and Ti. In another embodiment, the process can be carried out at a temperature ranging from 40° C. to 200° C. In another embodiment, the process can be carried out under pressure ranging from 1-10 bars.

In one embodiment, the process can be substantially free of isolation of one or more metal hydroxide(s). In other embodiment, the process can be substantially free of calcination step(s). In still other embodiment, the process can be substantially free of rigorous reduction step(s).

In one embodiment, the process can utilize Fehling's reagent B including a stoichiometric amount or an excess amount of sodium potassium tartrate with respect to the metal ions present in the mixed metal salt solution. In other embodiment, the process can utilize Fehling's reagent B including a sub-stoichiometric amount of sodium potassium tartrate with respect to the metal ions present in the mixed metal salt solution to induce defects and dislocations in the mixed metal oxide(s).

In one embodiment, mixed metal oxide(s) prepared according to embodiments of the present disclosure can be used as catalyst(s) for any or a combination of Methanol synthesis, DME synthesis, Fischer Tropsch synthesis and Water gas shift reaction. In other embodiment, mixed metal oxide(s) can be used for preparation of a bi-functional hybrid catalyst. In still other embodiment, the bi-functional hybrid catalyst can be highly selective for direct conversion of syn-gas to dimethyl ether (DME). In still other embodiment, bi-functional hybrid catalyst can further include a methanol dehydration component having one or more methanol dehydrating agent(s).

The present invention further relates to a highly selective bi-functional hybrid catalyst that can be used for direct conversion of syn-gas to dimethyl ether (DME) including:

(i) a methanol synthesis catalyst component consisting of Cu as an essential active metal in its intermediate oxidation state and one or more promoter metal(s) selected from Zn, Mg, Ni, Co, Ce, Ga, Al, Zr, Ca or Ti; and (ii) a methanol dehydration component consisting of one or more methanol dehydrating agents.

The present invention further relates to a process of producing a highly selective bi-functional hybrid catalyst for direct conversion of syn-gas to dimethyl ether (DME) including the steps of:

(i) precipitating a single metal or a mixed metal salt solution with Fehling's reagent B and glucose in presence of a metal complexing agent at suitable temperature to obtain one or more metal oxide(s) as catalyst wherein the metal can be selected from Copper, Zinc, Magnesium, Cerium, Gallium, Aluminium, Zirconium, Calcium, Nickel, Cobalt and Titanium.

(ii) mixing the one or more metal oxide(s) obtained from step (i) with one or more methanol dehydrating agents in a suitable weight ratio to prepare a hybrid catalyst; and (iii) contacting the hybrid catalyst as obtained from step (ii) with a gas mixture comprising carbon monoxide, hydrogen and/or carbon dioxide at a suitable temperature and pressure.

In another embodiment of the present invention, the metal salt solution can be selected from:

(i) salt solution of Copper;
(ii) salt solution of Zinc;
(iii) salt solution of a mixture of Copper and Zinc; or
(iv) a mixture of salt solution of Copper, Zinc and one or more metals selected from Mg, Ni, Co, Ce, Ga, Al, Zr, Ca or Ti.

In an embodiment of the present invention, the metal salt can be selected from nitrate, citrate and halide. In one embodiment, the complexing agent can be sodium potassium tartrate. In an embodiment of the present invention, the process includes the step of precipitating a metal salt solution with Fehling's reagent B and glucose to obtain metal oxide(s) as catalyst wherein the metal can be selected from Cu, Zn, Mg, Ni, Co, Ce, Ga, Al, Ca and Zr and the process can be carried out at a suitable temperature ranging from 40° C. to 200° C., more preferably 50° C. to 90° C.

In another embodiment of the present invention, mixing of metal oxide(s) with one or more methanol dehydrating agent(s) in a suitable weight ratio to prepare a hybrid catalyst can be done at a suitable temperature ranging from 40° C. to 200° C. In another embodiment of the present invention, contacting the hybrid catalyst with a gas mixture including carbon monoxide, hydrogen and/or carbon dioxide can be done at temperature ranging from 220° C. to 300° C. and pressure ranging from 30 to 50 bars.

In one embodiment, one or more methanol dehydrating agent(s) can be selected from alumina, silica-alumina, alumina-titania, alumina-zirconia or zeolite based materials.

The present invention further relates to a method for highly active and selective methanol synthesis by contacting the metal oxide catalyst as obtained in step (i) with syn-gas.

In an embodiment of the present invention, the process exhibits practical utility in the field of chemical and petrochemical industries for the production of methanol and dimethyl ether with high selectivity and higher yield value.

The process of metal oxide(s) synthesis of the present invention can also be utilized for producing several metal oxide based catalysts for converting syn-gas to methane, ethane, propane, butane, ethylene with high selectivity and yield in the direct syn-gas conversion.

The process(s) of the present invention can also be utilized to prepare metal oxide(s) which can be used either as catalyst carrier(s), adsorbent(s), drug-delivery carrier(s), abrasive(s), reactions sensors, glass, ceramics and coatings or as component thereof or in FCC and polymerization catalysis and various organic synthesis.

BRIEF DESCRIPTION OF THE DRAWINGS

For those skilled in the art, to understand the present disclosure numerous embodiments are described below, annexing drawings to minutely illustrate the matters of the disclosure and the purpose thereof.

DETAILED DESCRIPTION OF THE INVENTION

Figure 1:
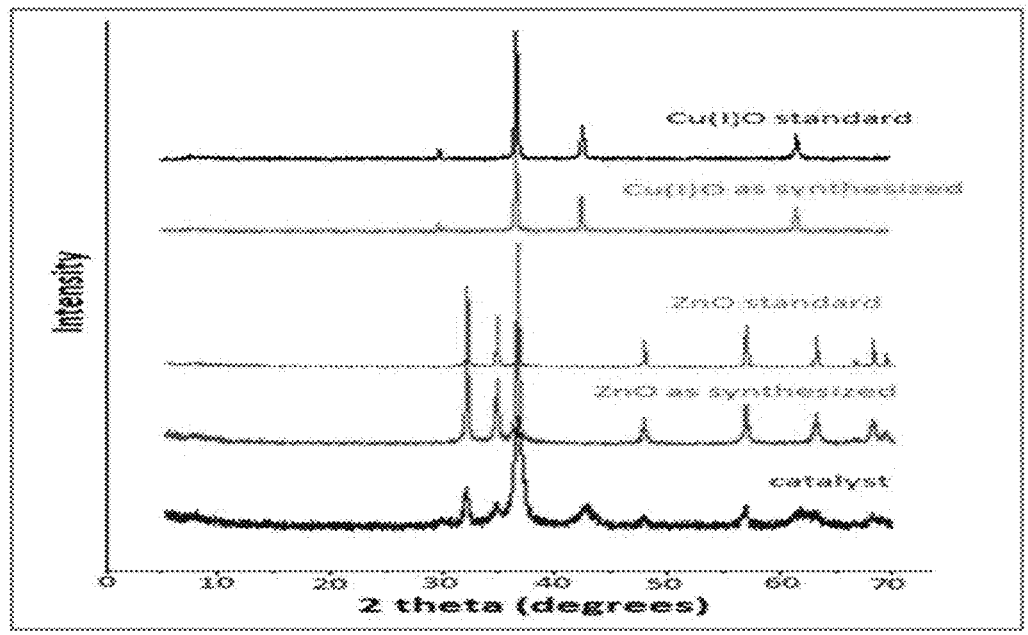
FIG. 1 illustrates the XRD patterns of the catalyst and its comparison to individual components of the catalysts, in accordance with present invention.

The embodiments herein and the various features and advantageous details thereof are explained more comprehensively with reference to the non-limiting embodiments that are detailed in the following description. Descriptions of well-known components and processing techniques are omitted so as to not unnecessarily obscure the embodiments herein.

Unless otherwise specified, all terms used in disclosing the invention, including technical and scientific terms, have the meaning as commonly understood by one of ordinary skill in the art to which this invention belongs. By means of further guidance, term definitions may be included to better appreciate the teaching of the present invention.

As used herein, the term "synthesis gas" or "syn-gas" refers to a gas mixture comprising carbon monoxide (CO) and hydrogen ($H_2$). The gas may also comprise carbon dioxide ($CO_2$). The relative amounts of the various components may differ.

As used herein, the term "calcination" refers to a thermal treatment process applied to ores and other solid materials to bring about a thermal decomposition, phase transition, or removal of a volatile fraction. The calcination process normally takes place at temperatures below the melting point of the product materials, and is done under an oxygen-containing atmosphere. In some cases, the calcination can be performed under an inert atmosphere (e.g. nitrogen).

As used in the description herein, the meaning of "a," "an," and "the" includes plural reference unless the context clearly dictates otherwise. Also, as used in the description herein, the meaning of "in" includes "in" and "on" unless the context clearly dictates otherwise.

As used herein, the terms "comprise", "comprises", "comprising", "include", "includes", and "including" are meant to be non-limiting, i.e., other steps and other ingredients which do not affect the end of result can be added. The above terms encompass the terms "consisting of" and "consisting essentially of".

As used herein, the terms "composition" "blend," or "mixture" are all intended to be used interchangeably.

The terms "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The present invention generally relates to in-situ preparation of mixed metal oxide(s) using glucose oxidation assisted precipitation through Fehling's route.

The present invention further relates to a process for in-situ preparation of mixed metal oxide(s) comprising the step of: precipitating a mixed metal salt solution with Fehling's reagent B and glucose at a suitable temperature; wherein said mixed metal salt solution comprises at least two metal ions; and
wherein half cell reduction potential of at least one metal ion of said at least two metal ions is lower than glucose.

In one embodiment, at least one metal ion can be selected from the group consisting of Zn, Mg, Ce, Ga, Al, Zr, Ca and Ti. In another embodiment, the process can be carried out at a temperature ranging from 40° C. to 200° C. In another embodiment, the process can be carried out under pressure ranging from 1-10 bars.

In one embodiment, the process can be substantially free of isolation of one or more metal hydroxide(s). In other embodiment, the process can be substantially free of calcination step(s). In still other embodiment, the process can be substantially free of rigorous reduction step(s).

In one embodiment, the process can utilize Fehling's reagent B including a stoichiometric amount or an excess amount of sodium potassium tartarate with respect to the metal ions present in the mixed metal salt solution. In other embodiment, the process can utilize Fehling's reagent B including a sub-stoichiometric amount of sodium potassium tartarate with respect to the metal ions present in the mixed metal salt solution to induce defects and dislocations in the mixed metal oxide(s).

In one embodiment, mixed metal oxide(s) prepared according to embodiments of the present disclosure can be used as catalyst(s) for any or a combination of Methanol synthesis DME synthesis, Fischer Tropsch synthesis and Water gas shift reaction. In other embodiment, mixed metal oxide(s) can be used for preparation of a bi-functional hybrid catalyst. In still other embodiment, the bi-functional hybrid catalyst can be highly selective for direct conversion of syn-gas to dimethyl ether (DME). In still other embodiment, bi-functional hybrid catalyst can further include a methanol dehydration component having one or more methanol dehydrating agent(s). In still other embodiment, one or more methanol dehydrating agent(s) can be selected from alumina, silica-alumina, alumina-titania, alumina-zirconia or zeolite based materials.

The present invention further relates to a highly selective bi-functional hybrid catalyst that can be used for direct conversion of syn-gas to dimethyl ether (DME) including:
(i) a methanol synthesis catalyst component consisting of Cu as an essential active metal in its intermediate oxidation state and one or more promoter metal(s) selected from Zn, Mg, Ni, Co, Ce, Ga, Al, Zr, Ca or Ti; and
(ii) a methanol dehydration component consisting of one or more methanol dehydrating agents.

The present invention further relates to a process of producing a highly selective bi-functional hybrid catalyst for direct conversion of syn-gas to dimethyl ether (DME) including the steps of:
(i) precipitating a single metal or a mixed metal salt solution with Fehling's reagent B and glucose at suitable temperature and pressure to obtain one or more metal oxide(s) as catalyst wherein the metal can be selected from Copper, Zinc, Magnesium, Cerium, Gallium, Aluminium, Zirconium, Calcium, Nickel, Cobalt and Titanium.
(ii) mixing the one or more metal oxide(s) obtained from step (i) with one or more methanol dehydrating agents in a suitable weight ratio to prepare a hybrid catalyst; and
(iii) contacting the hybrid catalyst as obtained from step (ii) with a gas mixture comprising carbon monoxide, hydrogen and/or carbon dioxide at a suitable temperature and pressure.

In another embodiment of the present invention, the metal salt solution can be selected from:
(i) salt solution of Copper;
(ii) salt solution of Zinc;
(iii) salt solution of a mixture of Copper and Zinc; or
(iv) a mixture of salt solution of Copper, Zinc and one or more metals selected from Mg, Ni, Co, Ce, Ga, Al, Zr, Ca or Ti.

In an embodiment of the present invention, the metal salt can be selected from nitrate, citrate and halide. In one embodiment, the metal complexing agent can be sodium potassium tartarate. In an embodiment of the present invention, the process includes the step of precipitating a metal salt solution with Fehling's reagent B and glucose to obtain metal oxide(s) as catalyst wherein the metal can be selected from Cu, Zn, Mg, Ni, Co, Ce, Ga, Al, Ca and Zr and the process can be carried out at a suitable temperature ranging from 40° C. to 200° C., more preferably 50° C. to 150° C. and most preferably 50° C. to 90° C.

In another embodiment of the present invention, mixing of metal oxide(s) with one or more methanol dehydrating agent(s) in a suitable weight ratio to prepare a hybrid catalyst can be done at a suitable temperature ranging from 40° C. to 200° C. In another embodiment of the present invention, contacting the hybrid catalyst with a gas mixture including carbon monoxide, hydrogen and/or carbon dioxide can be done at temperature ranging from 220° C. to 300° C. and pressure ranging from 30 to 50 bars.

The present invention further relates to a method for highly active and selective methanol synthesis by contacting the metal oxide catalyst as obtained in step (i) with syn-gas.

In an embodiment of the present invention, the process exhibits practical utility in the field of chemical and petrochemical industries for the production of methanol and dimethyl ether with high selectivity and higher yield value.

The process of metal oxide synthesis of the present invention can also be utilized for producing several metal oxide based catalysts for converting syn-gas to methane, ethane, propane, butane, ethylene with high selectivity and yield in the direct syn-gas conversion. Other applications of the metal oxide(s) prepared according to embodiments of the present invention can be found in Catal. Sci. Technol., 2012, 2, 1113-1125. Further, these mixed metal oxide(s) are important in inorganic technology and are widely used in diverse ceramic applications such as refractories, ferroelectric devices, as inorganic pigments and the like. Of particular interest is the use of mixed metal oxides as inorganic pigments for applications in ceramics, paint and plastics. It would be appreciated that the metal oxide(s) prepared according to embodiments of the present disclosure can be utilized for variety of applications as known to a person skilled in the art including but not limited to as catalyst carrier(s), adsorbent(s), drug-delivery carrier(s), abrasive(s), reactions sensors, glass, ceramics and coatings or as component thereof or in FCC and polymerization catalysis and various organic synthesis.

In an embodiment of the present invention, the Fehling's reagent B is solution of sodium potassium tartrate and sodium hydroxide in distilled water.

In another embodiment of the present invention, the complexing agent can be added to a bulk solution of active metal or added simultaneously during mixed metal oxide synthesis process.

In one exemplary embodiment, the method of the present invention produces Cu-oxide(s) directly in the form cuprous oxide Cu(I)O, but not cupric oxide that results in much higher selectivity for methanol as well as dimethyl ether synthesis when coupled with one or more methanol dehydrating agent(s). This eliminates the rigorous hydrogen reduction procedure of first converting the Cu(II) oxide to Cu(I) and then to Cu(0).

In another embodiment, the present bi-functional hybrid catalyst for direct conversion of syn-gas to DME can withstand the severe process conditions and resist the coke formation process during syngas conversion to DME.

In another embodiment, the present bi-functional catalyst exhibits high selectivity and high yield against methanol and dimethyl ether production from syn-gas.

In another embodiment of the present invention provides, copper crystallite produced has lower particle size distribution and higher active surface area. Hence, the reaction rate can easily be controlled through tuning reaction temperature.

The conversion of CO can be calculated using the following formula:

Conversion of CO (mol %) =

$$\frac{(\text{inlet moles of CO} - \text{outlet moles of CO})}{\text{inlet moles of CO}} \times 100$$

The selectivity can be calculated using the following formula:

$$\text{Selectivity (mol \%)} = \frac{n_i \times \text{moles of produced component}}{(\text{inlet moles of CO} - \text{outlet moles of CO})} \times 100$$

(where $n_i$ is the stoichiometric coefficient for each of the product produced)

The yield percentage of DME can be calculated using the following formula:

$$\text{Yield of DME (mol \%)} = \frac{\text{CO conversion} \times \text{DME selectivity}}{100}$$

In an embodiment, the present invention produces methanol and dimethyl ether with high selectivity by using a solid catalyst comprising copper with second and third catalyst component selected from Zn, Ga, Al, Ca, Mg or Zr.

The method of metal oxide(s) synthesis of the present invention can also be utilized for producing several metal oxide based catalyst for converting syn-gas to methane, ethane, propane, butane, ethylene with high selectivity in direct syn-gas conversion.

Referring to FIG. 1, the metal oxide(s) of Cu and Zn was prepared by a glucose oxidation assisted precipitation method using the concept of in-situ reduction of $Cu^{2+}$ in accordance with the embodiments of the present disclosure.

In a preferred embodiment of the present invention, the mixed metal solution of copper and zinc was prepared by dissolving the respective nitrate salts in approximately 1-2 litres of distilled water. Simultaneously, Fehling's solution B was prepared by dissolving appropriate amount of sodium potassium tartarate (complexing agent for metals) and NaOH in distilled water. Both the solutions were then mixed in a three neck round bottom flask attached with a condenser. The contents of the flask were heated at a temperature of 70-90° C. and the whole system was maintained at the same condition for appropriate time. Then, the contents were allowed to cool naturally. The final pH was measured to be 8.0-9.0 after the completion of the process. The precipitate was then filtered and washed several times with distilled water to remove residual sodium ions. Removability of the Na+ or any other ion was confirmed by conductivity measurement of the filtrate. Washing was continued till the conductivity equals to that of pure distilled water. It was dried overnight and the solid was then obtained.

In an embodiment of the present invention, FIG. 1 refers to XRD patterns of the metal oxide(s) synthesized according to embodiments of the present disclosure. To confirm that the precipitation of the catalyst occurred in the form of cuprous oxide but not cupric oxide, the catalyst synthesis procedure was applied to nitrate solution containing separately copper salt only and similarly containing zinc salt only. The XRD pattern of material was then compared with the XRD pattern of standard cuprous oxide and zinc oxide structure respectively. It was confirmed that the desired metals were obtained directly in the form of oxides and that too in the form of cuprous oxide and not cupric oxide.

For comparison purpose, one more metal oxide(s) with same composition were prepared using the same route through conventional co-precipitation method but in a jacketed reactor where drop wise addition of both solutions (nitrate and Fehling's B) took place. After precipitation, the precipitates were aged for 1 hour at the same temperature under continuous stirring. Filtration and washing techniques were employed as previous. The way of adding both the solutions, the metal nitrate solution and the Fehling B solution, can be altered. The solutions can be added in the following manner:

1. Both the solutions can be added simultaneously in the jacketed reactor having glucose and water.
2. One of the solutions can be taken in the jacketed reactor along with the glucose and water and other can be added externally
3. Glucose and one of the solutions can be added externally having other solution in the reactor.

There are many ways of adding these solutions and precipitating out the metal oxide(s). The person skilled in the art may perform the mixed metal oxide(s) synthesis in many interesting ways by playing with the different synthesis parameters and various compositions of metals within the mixed metal oxide so as to obtain the metal oxide(s) with different physico chemical properties. This methodology provides precipitation of metal oxide(s) at relatively lower temperature. One can also use sub-stoichiometric amount of the complexing agent or glucose or pH maintaining agent (NaOH) so that more than one metal species can co-exist within the same mixed metal oxide unit because then not whole of the metal can get complexed and reduced. This will create non-uniformity in the mixed metal oxide thereby inducing defects and uneven crystal structure. This further improves the catalytic performance and efficiency as defects are the majorly responsible for the catalytic activity of any material.

For another comparison with conventional method of metal oxide(s) synthesis, the mixed metal oxide was prepared using conventional co-precipitation technique. In typical synthesis, the mixed solutions of copper and zinc nitrate and an aqueous solution of $Na_2CO_3$ were added drop wise to the jacketed reactor containing distilled water, under continuous stirring. The pH was maintained at 7.0 during precipitation by controlling the flow rates of two solutions. The mixed metal oxide thus obtained was subjected to the catalytic activity test under various conditions to verify its applicability for the process of syn-gas conversion to DME. The catalytic activity of all bi-functional hybrid catalysts were tested by using a high pressure fixed bed tubular reactor. Typically, 12-20 g of catalyst in the form of oxide pellet (450-600 microns) was placed in the middle of the reactor tube. The test reactor set up was equipped with a gas feeding system, tubular furnace, mass flow controllers (MFC), back pressure regulator, product recovery and separation system and a gas outflow measuring section.

Before the activity test, the loaded catalyst in the reactor was subjected to a one stage activation process in which the catalyst was reduced with a stream of pure $H_2$ at 300° C. for appropriate time. $H_2$ and CO gases in 1.5:1 ratio were fed into the reactor through separate mass flow controllers. As the feed stream passed through the inert beds, it was heated to achieve the desired temperature. Effluent stream leaving from the bottom of the reactor passed through a condenser to a product separator. Condensed liquid product stream was separated from the non-condensable gases in the separator. A back pressure regulator (BPR) was placed in the separator to regulate the system pressure. The gaseous effluents leaving the separator through the BPR passed through a wet gas meter, which measured the volumetric flow rate. Most of the reactions were performed under the operating reactor pressure of 30 bars with a space velocity of 2000 ml/gcat·hr and at 240° C. The experiments were also performed by varying the reaction temperature and pressure in the range of 240-260° C. and 30-50 bar respectively.

In a preferred embodiment, the catalyst comprising copper may contain copper metal, with one or more of the other metals, such as zinc, zirconium etc. and also with or without one or more promoter metal oxides, such as magnesium, calcium and also dehydration agents for methanol such as alumina etc. in the form of powder, pellets or may be incorporated in the form of solution during the catalyst synthesis procedure only.

In a preferred embodiment of the present invention, the salt comprising Cu metal is copper nitrate, the salt comprising zinc is zinc nitrate and the salt containing magnesium is magnesium nitrate. Alumina as a dehydration agent is preferred in the form of aluminum oxide, added physically to the precipitated catalyst. In an embodiment of the present invention, during the process of synthesis of DME from syn-gas, step (i) is critical. In step (i), alkaline solution of Fehling's reagent makes a complex with metal ions of the nitrate solutions so as to prevent them from getting precipitated in the form of hydroxides or hydroxycarbonate as catalyst precursor. This complex is known as metal-tartrate complex. Careful performance of this step is required to get the precipitates directly in the form of oxides. These oxides are obtained as a result of controlled release of metal ions from the tartrate complex and their simultaneous reduction from higher oxidation state to lower oxidation state via glucose oxidation in case half cell reduction potential of one of the metal is higher than glucose. Strikingly, metals with half cell reduction potential lower than glucose can also be precipitated according to embodiments of the present disclosure directly into their corresponding oxide, the only difference being non-reduction of the metal precursor during the process.

Many tartrate salts are available for preparation of these kinds of complexes but a watchful selection is needed so as to ensure that the metal should form a complex with the tartrate and not with its counter ions because Cu metal is known to form many co-ordination complexes like with ammonium ions etc. which could be more stable than the corresponding tartrate complexes.

While certain embodiments have been shown and described, various modifications and substitutions may be made thereto without departing from the spirit and scope of the disclosure. Therefore, it is to be understood that the present disclosure has been described by way of illustration and not limitations.

Advantages of the Invention

The present invention provides a process for preparing mixed metal oxide(s) capable of eliminating the necessity of isolation of metal hydroxide(s).

The present invention provides a process for preparing mixed metal oxide(s) capable of eliminating calcinations and heating at high temperature.

The present invention provides a process for preparing mixed metal oxide(s) capable of eliminating rigorous reduction step(s).

The present invention provides a facile synthetic route to diverse metal oxide based catalyst(s).

The present invention provides a catalyst component of the hybrid catalyst for the conversion of syn-gas to methanol.

The present invention provides a highly selective bi-functional hybrid catalyst for direct conversion of syn-gas to dimethyl ether (DME).

The present invention provides a process for preparing a bi-functional catalyst wherein the metal oxide is in an intermediate oxidation state, for example, copper oxide is in the form of cuprous oxide [Cu(I)O] instead of cupric oxide [Cu(II)O].

The present invention provides a method of preparation of a superior bi-functional catalyst for direct conversion of syn-gas to DME which can withstand the severe process conditions and resist the coke formation process during syngas conversion to DME.

The present invention provides a process for preparing a bi-functional catalyst capable of exhibiting high stability against sintering and deactivation.

The present invention provides a process for preparing a bi-functional catalyst capable of exhibiting high selectivity and yield against methanol and dimethyl ether production.

The present invention provides a process for preparing a bi-functional catalyst capable of involving low process parameter of pressure and temperature.

The present invention provides a process for preparing mixed metal oxide(s) which obviates the disadvantages associated with known art.

The present invention provides a process for preparing mixed metal oxide(s) which is inexpensive, dependable and fully effective in accomplishing its intended purposes.

The present invention provides a process that is technically and commercially feasible.

EXAMPLES

The present invention is further explained in the form of following examples illustrating the metal oxide(s) synthesis procedures of this invention and its utilization as catalyst(s) in DME synthesis. Drastic improvement in the selectivity and yield of dimethyl ether in the process of directly converting syn-gas to dimethyl ether (DME) utilizing a solid catalyst essentially comprising copper, prepared according to embodiments of the present disclosure, would be apparent from one or more examples provided herein below. However, it is to be understood that the foregoing examples are merely illustrative and are not to be taken as limitations upon the scope of the invention. Various changes and modifications to the disclosed embodiments will be apparent to those skilled in the art. Such changes and modifications may be made without departing from the scope of the invention.

Example 1: Synthesis of Highly Selective Bi-functional Hybrid Catalyst of the Present Invention This example illustrates the method of catalyst synthesis of this invention for drastically improving the selectivity and yield of dimethyl ether synthesis in the process of directly converting syn-gas to dimethyl ether (DME) over a solid catalyst essentially comprising Copper containing hybrid catalyst along with $\gamma$-$Al_2O_3$ as methanol dehydration agent.

The method was carried out in three steps:

Step (i): Mixed metal nitrate solution was prepared by mixing nitrate salts of copper and zinc in an aqueous solution of about 1000 ml wherein, the mol percentages of Cu and Zn range from 40-60% and 30-50% respectively. Another solution was made by mixing sodium potassium tartrate and sodium hydroxide in proper molar ratio in an aqueous solution of about 500 ml. Both the solutions were then simultaneously added to a jacketed reactor under continuous stirring with controlled flow rates. Precipitates obtained were then filtered and washed several times with distilled water to ensure complete removal of the residual ions. After washing, precipitates were dried at around 80° C. overnight.

Step (ii): The dried precipitates were then mixed physically with methanol dehydration agent in the ratio of 2:1 and pelletized in a KBr pelletizer.

Step (iii): The solid catalyst thus obtained from step (ii) was then reduced under hydrogen and contacted with a gas mixture consisting of carbon monoxide and hydrogen in a fixed bed or slurry reactor.

TABLE 1

Catalyst synthesis and catalyst testing conditions

| Catalyst synthesis conditions | |
| --- | --- |
| Reactor capacity (cm³) | 3000 |
| Volume of water (cm³) | 800 |
| Volume of nitrates containing solution (ml) | 1000 |
| Concentration of nitrate solutions | 0.5M |
| Volume of carbonate containing solution (ml) | 500 |
| Concentration of tartrate/carbonate solution | 1.0M |
| pH | 7.0-9.0 |
| Flow rate of nitrate solution (ml/min) | 20 |
| Flow rate of tartrate/carbonate solution (ml/min) | 10 |
| RPM of the agitator | 350 |
| Synthesis temperature (° C.) | 70 |
| Pressure (atm) | atm |
| Synthesis duration (h) | 3.5 |
| Aging time (h) | 1 |
| Aging temperature (° C.) | 20-90 |
| Catalyst testing conditions | |
| Reducing gas | 100% $H_2$ |
| Reduction duration (h) | 5 |
| Temperature (° C.) | 240 |
| Pressure (bars) | 30-50 |
| $H_2$ flow rate (NLPH) | 12 |
| CO flow rate (NLPH) | 8 |
| $H_2$/CO ratio | 1.5 |
| WHSV of synthesis gas (H2 + CO) (ml/gcat · hr) | 2000 |

(The flow rates of the gases were measured at room temperature and atmospheric pressure. Weight hourly space velocity (WHSV) is a volume of gas passed through the reactor per unit mass of catalyst per hour.)

After obtaining the catalyst from step (ii), step (iii) was performed. The conversion and selectivities in each of the further examples are calculated on the basis of mol %. The results obtained are as follows:

Conversion of CO (mol %)=45.04%
Selectivity of Products (Mol %):
DME selectivity=60.29%
$CO_2$ selectivity=24.79%
$CH_4$ selectivity=7.06%
C2+ selectivity=7.86%
Yield of DME=27.1%

Figure 2:
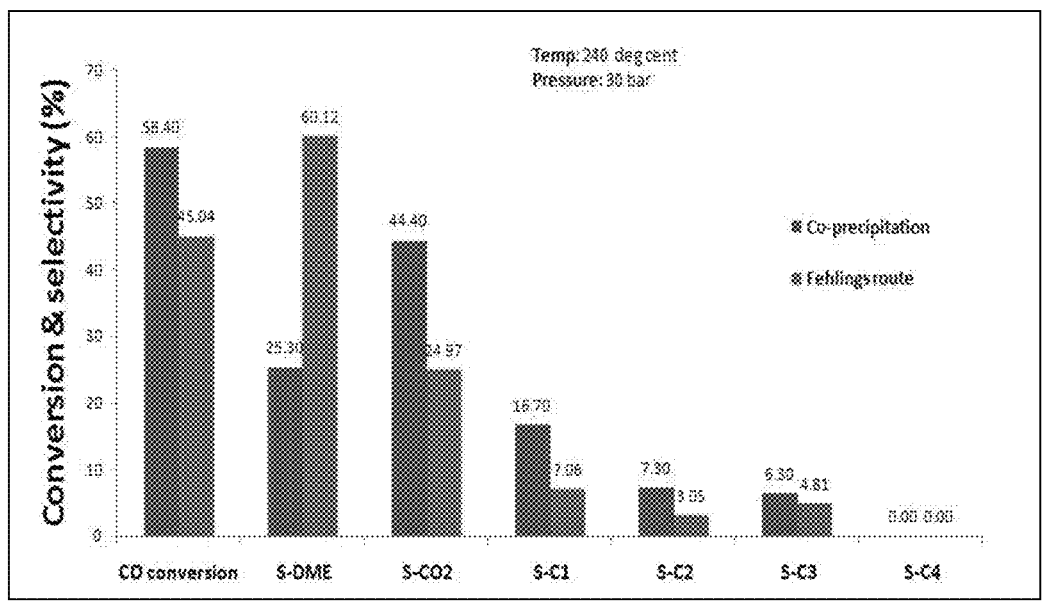
FIG. 2 illustrates the comparison chart between the catalytic activities of the catalysts synthesized through conventional route and through the present invention

Example 2: Comparison of Process of Preparing Bi-functional Hybrid Catalyst of the Present Invention with Respect to a Known Conventional Method In this example, the method of invention was compared with the conventionally established method of catalyst synthesis for direct conversion of syn-gas to DME. The catalyst was prepared through conventional co-precipitation method, calcined and then reduced in the atmosphere of hydrogen. The composition of the catalyst was exactly the same as described in Example 1. In all the experiments, temperature, pressure, $H_2$/CO ratio and WHSV were kept constant and the experiments were performed under the conditions described in Example 1. The comparison results are presented in Table 2 and FIG. 2.

TABLE 2

Comparison between the activity data of the catalyst synthesized from the conventional route and the route of present invention

| Results of syn-gas to DME conversion | Example 1 | Example 2 |
|---|---|---|
| Syn-gas conversion | 45.04 | 58.4 |
| DME selectivity | 60.29 | 25.3 |
| Methanol selectivity | 0.0 | 0.0 |
| $CO_2$ selectivity | 24.79 | 44.4 |
| Methane selectivity | 7.06 | 16.7 |
| C2+ selectivity | 7.86 | 13.6 |
| DME yield | 27.1 | 14.8 |

The results in Example 2 show that the present method of invention drastically increased the DME yield and selectivity. Also, the by-product $CO_2$ formation was also decreased significantly.

Example 3

This example further illustrates the method of catalyst synthesis of this invention for drastically improving the selectivity for dimethyl ether in the process of directly converting syn-gas to dimethyl ether (DME) over solid acid catalyst comprising MgO along with copper and zinc. The method of invention was carried out in three steps as described in Example 1, except that the solid catalyst comprises Mg which was included in the form of nitrate and precipitated out in the form of MgO along with $Cu_2O$ and ZnO. The composition of the catalyst contained 40-60% by weight of Cu, 15-50% by weight of Zn and 10-30% by weight of Mg. All the elements are in the mole ratios. In all the experiments, temperature, pressure, $H_2$/CO ratio and WHSV were kept constant and activity runs were performed according to the conditions explained in Example 1. The results of the activity of the catalyst are summarized in Table 3 and compared with the catalyst prepared in Example 1 which was not promoted by MgO.

TABLE 3

Comparison between the catalytic activities of the catalysts synthesized using the route of present invention

| Results of Syn-gas to DME conversion | Example 1 | Example 3 |
|---|---|---|
| Syn-gas conversion | 45.04 | 56.08 |
| DME selectivity | 60.29 | 72.06 |
| Methanol selectivity | 0.0 | 0.0 |
| $CO_2$ selectivity | 24.79 | 18.4 |
| Methane selectivity | 7.06 | 5.6 |
| C2+ selectivity | 7.86 | 5.9 |
| DME yield | 27.1 | 40.41 |

Examples 4 to 6

These examples further illustrate the method of catalyst synthesis of this invention for drastically improving the selectivity for dimethyl ether in the process of directly converting syn-gas to dimethyl ether (DME) over a solid catalyst essentially comprising copper and zinc containing hybrid catalyst along with γ-$Al_2O_3$ as a methanol dehydration agent.

In these examples, different process conditions for direct conversion of syn-gas to DME were explained using the catalyst synthesized as described in Example 1. The examples illustrate the effect of temperature variation at 30 bar pressure on the conversion pattern of CO, selectivity and yield patterns of DME and other products. The pressure, $H_2$/CO ratio and WHSV were kept constant in all the experiments in Examples 4-6. The results are summarized in Table 4.

TABLE 4

Effect of temperature on CO conversion and DME selectivity

|  | Example 1 | Example 4 |
|---|---|---|
| Catalyst testing conditions |  |  |
| Reducing gas | 100% $H_2$ | 100% $H_2$ |
| Reduction duration (h) | 5 | 5 |
| Temperature (° C.) | 240 | 220 |
| Pressure (bars) | 30 | 30 |
| $H_2$ flow rate (NLPH) | 12 | 12 |
| CO flow rate (NLPH) | 8 | 8 |
| $H_2$/CO ratio | 1.5 | 1.5 |
| WHSV of synthesis gas ($H_2$ + CO) (ml/gcat · hr) | 2000 | 2000 |
| Results of syn-gas to DME conversion |  |  |
| Syn-gas conversion | 45.04 | 17.73 |
| DME selectivity | 60.29 | 67.45 |
| Methanol selectivity | 0.0 | 0.0 |
| $CO_2$ selectivity | 24.79 | 15.87 |
| Methane selectivity | 7.06 | 8.47 |
| C2+ selectivity | 7.86 | 7.89 |

|  | Example 5 | Example 6 |
|---|---|---|
| Catalyst testing conditions |  |  |
| Reducing gas | 100% $H_2$ | 100% $H_2$ |
| Reduction duration (h) | 5 | 5 |
| Temperature (° C.) | 260 | 280 |
| Pressure (bars) | 30 | 30 |
| $H_2$ flow rate (NLPH) | 12 | 12 |
| CO flow rate (NLPH) | 8 | 8 |
| $H_2$/CO ratio | 1.5 | 1.5 |
| WHSV of synthesis gas ($H_2$ + CO) (ml/gcat · hr) | 2000 | 2000 |
| Results of syn-gas to DME conversion |  |  |
| Syn-gas conversion | 49.86 | 55.40 |
| DME selectivity | 31.42 | 22.31 |
| Methanol selectivity | 0.0 | 0.0 |
| $CO_2$ selectivity | 38.02 | 43.62 |
| Methane selectivity | 15.57 | 18.28 |
| C2+ selectivity | 8.41 | 15.79 |

Examples 7 to 12

This example further illustrates the method of catalyst synthesis of this invention for drastically improving the selectivity and yield of dimethyl ether synthesis in the process of directly converting syn-gas to dimethyl ether (DME) over a solid catalyst essentially comprising Copper and zinc containing hybrid catalyst along with γ-$Al_2O_3$ as a methanol dehydration agent.

In these examples, different process conditions for direct conversion of syn-gas to DME were explained using the catalyst synthesized as described in Example 1. The examples illustrate the effect of temperature variation at 50 bar pressure on the conversion pattern of CO, selectivity and yield patterns of DME and other products. The pressure, $H_2$/CO ratio and WHSV were kept constant in all the experiments in Examples 7-12. The results are summarized in Table 5.

TABLE 5

Effect of temperature on CO conversion and DME selectivity

|  | Example 7 | Example 8 |
|---|---|---|
| Catalyst testing conditions |  |  |
| Reducing gas | 100% $H_2$ | 100% $H_2$ |
| Reduction duration (h) | 5 | 5 |
| Temperature (° C.) | 200 | 220 |
| Pressure (bars) | 50 | 50 |
| $H_2$ flow rate (NLPH) | 12 | 12 |
| CO flow rate (NLPH) | 8 | 8 |
| $H_2$/CO ratio | 1.5 | 1.5 |
| WHSV of synthesis gas ($H_2$ + CO) (ml/gcat · hr) | 2000 | 2000 |
| Results of syn-gas to DME conversion |  |  |
| Syn-gas conversion | 15.15 | 17.14 |
| DME selectivity | 90.71 | 70.81 |
| Methanol selectivity | 0.0 | 0.0 |
| $CO_2$ selectivity | 5.0 | 18.75 |
| Methane selectivity | 0.29 | 4.35 |
| C2+ selectivity | 0.0 | 6.07 |
|  | Example 9 | Example 10 |
| Catalyst testing conditions |  |  |
| Reducing gas | 100% $H_2$ | 100% $H_2$ |
| Reduction duration (h) | 5 | 5 |
| Temperature (° C.) | 240 | 260 |
| Pressure (bars) | 50 | 50 |
| $H_2$ flow rate (NLPH) | 12 | 12 |
| CO flow rate (NLPH) | 8 | 8 |
| $H_2$/CO ratio | 1.5 | 1.5 |
| WHSV of synthesis gas ($H_2$ + CO) (ml/gcat · hr) | 2000 | 2000 |
| Results of syn-gas to DME conversion |  |  |
| Syn-gas conversion | 73.72 | 76.62 |
| DME selectivity | 25.97 | 23.18 |
| Methanol selectivity | 0.0 | 0.0 |
| $CO_2$ selectivity | 42.28 | 43.04 |
| Methane selectivity | 14.80 | 16.75 |
| C2+ selectivity | 16.3 | 17.01 |
|  | Example 11 | Example 12 |
| Catalyst testing conditions |  |  |
| Reducing gas | 100% $H_2$ | 100% $H_2$ |
| Reduction duration (h) | 5 | 5 |
| Temperature (° C.) | 280 | 300 |
| Pressure (bars) | 50 | 50 |
| $H_2$ flow rate (NLPH) | 12 | 12 |
| CO flow rate (NLPH) | 8 | 8 |
| $H_2$/CO ratio | 1.5 | 1.5 |
| WHSV of synthesis gas ($H_2$ + CO) (ml/gcat · hr) | 2000 | 2000 |
| Results of syn-gas to DME conversion |  |  |
| Syn-gas conversion | 75.78 | 78.25 |
| DME selectivity | 27.74 | 25.30 |
| Methanol selectivity | 0.0 | 0.0 |
| $CO_2$ selectivity | 44.21 | 42.32 |
| Methane selectivity | 14.94 | 17.48 |
| C2+ selectivity | 13.09 | 14.9 |

Examples 13 to 14

This example further illustrates the method of catalyst synthesis of this invention for drastically improving the selectivity and yield of dimethyl ether synthesis in the process of directly converting syn-gas to dimethyl ether (DME) over a solid catalyst essentially comprising Copper and zinc containing hybrid catalyst along with γ-$Al_2O_3$ as a methanol dehydration agent.

In these examples, different process conditions for direct conversion of syn-gas to DME were explained using the catalyst synthesized as described in Example 1. The examples illustrate the effect of WHSV variation at 30 bar pressure on the conversion pattern of CO, selectivity and yield patterns of DME and other products. The temperature, pressure and $H_2$/CO ratio and were kept constant in all the experiments in Examples 13-14. The results are summarized in Table 6 and are compared with Example 1.

TABLE 6

Effect of WHSV on CO conversion and DME selectivity

|  | Example 1 | Example 13 | Example 14 |
|---|---|---|---|
| Catalyst testing conditions |  |  |  |
| Reducing gas | 100% $H_2$ | 100% $H_2$ | 100% $H_2$ |
| Reduction duration (h) | 5 | 5 | 5 |
| Temperature (° C.) | 240 | 240 | 240 |
| Pressure (bars) | 30 | 30 | 30 |
| $H_2$ flow rate (NLPH) | 12 | 12 | 12 |
| CO flow rate (NLPH) | 8 | 8 | 8 |
| $H_2$/CO ratio | 1.5 | 1.5 | 1.5 |
| WHSV of synthesis gas ($H_2$ + CO) (ml/gcat · hr) | 2000 | 2500 | 3000 |
| Results of syn-gas to DME conversion |  |  |  |
| Syn-gas conversion | 45.04 | 48.30 | 50.27 |
| DME selectivity | 60.29 | 55.42 | 44.62 |
| Methanol selectivity | 0.0 | 0.0 | 0.0 |
| $CO_2$ selectivity | 24.79 | 28.87 | 38.79 |
| Methane selectivity | 7.06 | 8.47 | 9.06 |
| C2+ selectivity | 7.86 | 7.89 | 7.86 |

We claim:

1. A process for in-situ preparation of a mixed metal oxide comprising: effecting mixing of a mixed metal salt solution with Fehling's reagent B and glucose at a suitable temperature to afford precipitates of the mixed metal oxide, wherein said mixed metal salt solution comprises at least two metal ions, and wherein half-cell reduction potential of at least one metal ion of said at least two metal ions is lower than glucose, further wherein the process utilizes sub-stoichiometric amount of any of Fehling's reagent B and glucose with respect to metal ions present in the mixed metal salt solution.

2. The process as claimed in claim 1, wherein the process is substantially free of isolation of one or more metal hydroxide(s).

3. The process as claimed in claim 1, wherein the process is substantially free of calcination step(s).

4. The process as claimed in claim 1, wherein said at least one metal ion is selected from the group consisting of Zn, Mg, Ce, Ga, Al, Zr, Ca or Ti.

5. The process as claimed in claim 1, wherein the temperature for carrying out the process ranges from 40° C. to 200° C.

6. The process as claimed in claim 1, wherein the process is carried out under pressure ranging from 1-10 bars.

* * * * *